United States Patent [19]

Oosta et al.

[11] Patent Number: 5,725,480
[45] Date of Patent: Mar. 10, 1998

[54] NON-INVASIVE CALIBRATION AND CATEGORIZATION OF INDIVIDUALS FOR SUBSEQUENT NON-INVASIVE DETECTION OF BIOLOGICAL COMPOUNDS

[75] Inventors: Gary M. Oosta, Gurnee; Tuan A. Elstrom, Lake Bluff; Eric B. Shain, Glencoe, all of Ill.; Thomas G. Schapira, Bristol, Wis.

[73] Assignee: Abbott Laboratories, Abbott Park, Ill.

[21] Appl. No.: 611,912

[22] Filed: Mar. 6, 1996

[51] Int. Cl.$^6$ .................................................. A61B 8/14
[52] U.S. Cl. ................................... 600/310; 600/556
[58] Field of Search ............................ 128/743, 633, 128/664–66, 653

[56] References Cited

U.S. PATENT DOCUMENTS

| | | | |
|---|---|---|---|
| 4,528,985 | 7/1985 | Macovski | 128/653 |
| 5,204,532 | 4/1993 | Rosenthal | 250/341 |
| 5,348,003 | 9/1994 | Caro | |
| 5,519,208 | 5/1996 | Esparza et al. | 128/664 |

FOREIGN PATENT DOCUMENTS

| | | |
|---|---|---|
| 19512478 | 3/1996 | Germany |
| 9300855 | 1/1993 | WIPO |
| 9506431 | 3/1995 | WIPO |

OTHER PUBLICATIONS

R.R. Anderson, et al., "The Optics of Human Skin", *The Journal of Investigative Dermatology*, vol. 77, No. 1 (1981), pp. 13–19.

S. Fantini, et al., "Quantitative determination of the absorption spectra of chromophores in strongly scattering media: a light-emitting-diode based technique", *Applied Optics*, vol. 33, No. 22, 1 Aug. 1994, pp. 5204–5213.

N. Kollias, et al., "Spectroscopic Characteristics of Human Melanin In Vivo", *The Journal of Investigative Dermatology*, vol. 85, No. 1, (1985), pp. 38–42.

N. Kollias, et al., "On The Assessment of Melanin in Human Skin *in vivo*", *Photochemistry and Photobiology*, vol. 43, No. 1, (1986), pp. 49–54.

Primary Examiner—Max Hindenberg
Assistant Examiner—Pamela L. Wingood
Attorney, Agent, or Firm—David L. Weinstein; Gregory W. Steele

[57] ABSTRACT

A process of calibrating an individual in preparation for the non-invasive measurement of an biological compound across the skin of that individual using non-ionizing radiation is provided. The process includes determining the contribution of one or more skin parameters to the absorption and transmittance data and correcting the subsequent non-invasive measurement of the biological compound for the contribution of the parameter(s).

10 Claims, 1 Drawing Sheet

NON-INVASIVE CALIBRATION AND CATEGORIZATION OF INDIVIDUALS FOR SUBSEQUENT NON-INVASIVE DETECTION OF BIOLOGICAL COMPOUNDS

FIELD OF THE INVENTION

The field of this invention is the non-invasive determination of biological compounds. More particularly, this invention pertains to the correction of such non-invasive measurements using calibration measurements of skin parameters.

BACKGROUND OF THE INVENTION

There are numerous existing methods for the non invasive detection and monitoring of biologically significant compounds in a subject. Typically, such methods measure the effect of the compound on the absorbance, reflectance or transmittance of non-ionizing radiation that illuminates a portion of the subject. In all such existing non-invasive methods, the illuminating and reflected/transmitted non-ionizing radiation must pass through the skin of the subject.

None of the existing methods provide a procedure whereby the variability of absorbance, reflectance or transmission due to skin parameters on the nonionizing radiation are calibrated and used to correct the measurement of the biologically significant compound. Variations due to skin parameters can result from genetic and environment factors, which factors are not only unique to a given subject but which factors may change in the same individual over time.

Two approaches for calibrating and correcting noninvasive measurements of biological compounds have been proposed. One approach, directed to the detection of glucose, suggests that each subject be calibrated individually by correlating measurements through tissue with whole blood samples from a glucose tolerance test.

A second approach contemplates a universal calibration system. The assumption behind this second approach is that all subject variability is accounted for by making a sufficiently large number of calibration measurements to define a single (universal) calibration line. It is unlikely, however, that a universal calibration line will reduce individual variability to levels currently achieved with invasive measurement methods.

Thus, there continues to be a need to provide an accurate, efficient, easy-to-use calibration and correction procedure for use in the non-invasive detection of biological compounds.

SUMMARY OF THE INVENTION

Figure 1:
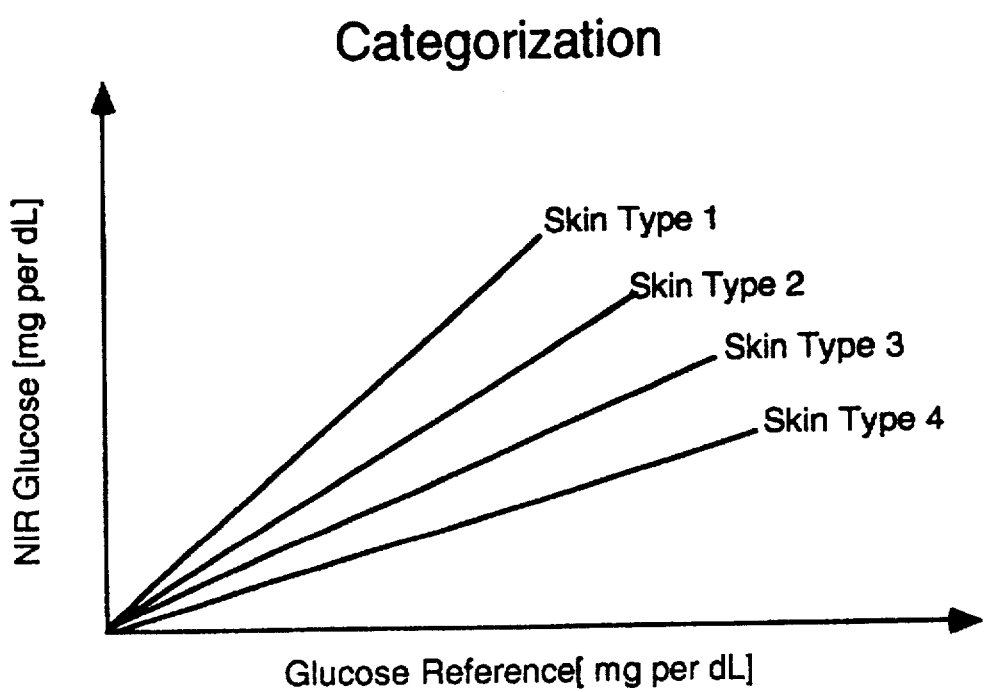
FIG. 1 shows a reference glucose value determined by an invasive reference method (y-axis) as a function of the in-vivo glucose value determined by a noninvasive method (x-axis). Separate calibration lines are used for different skin types.

The present invention provides a process of calibrating an individual in preparation for the non-invasive measurement of a biological compound across the skin of that individual wherein the contribution of one or more skin parameters to the non-invasive measurement is used to correct the subsequent non-invasive measurement of the biological compound for the contribution of the one or more skin parameters. Preferred skin parameters are melanin, or other chromophores such as hemoglobin, skin thickness, water content, and blood flow; most preferred is melanin. A preferred process is the correction of the contribution of melanin, or other chromophores such as hemoglobin, to the non-invasive measurement of glucose. In this embodiment, the contribution of melanin to the absorption and transmittance of non-ionizing radiation is accomplished by determining the absorption and scattering coefficients of melanin. Preferably, the absorption and scattering coefficients of melanin, or other chromophores such as hemoglobin, are determined using diffuse reflective or frequency domain measurements of melanin, or other chromophores such as hemoglobin.

Most preferably, the process of the invention is utilized immediately before the non-invasive measurement of the biological compound. Alternatively, the process of the invention may be stored in a device or instrument, e.g. as a "factory calibration".

DETAILED DESCRIPTION OF PREFERRED EMBODIMENTS

The term "analyte", "biologically significant compound" or "biological compound" means any chemical or elemental compound of clinical and/or medical, environmental, or industrial significance and for which quantitative or qualitative measurements may be desired. Examples of specific analytes or components of biological interest are well known and include analytes of clinical significance as glucose, hemoglobin, lipids, cholesterol, protein, etc. Other analytes will be readily apparent to those skilled in the art. A preferred biological compound is glucose.

The term "skin parameters" means those features which are relevant to the correlation error of the biological compound of interest. Skin parameters which are known or believed to be relevant to the correlation error calculation include, but are not limited to, melanin content, chromophores (e.g., hemoglobin, bilirubin, carotenoids, amino acids), water content of the skin, fat content, temperature, skin quality, blood flow, skin elasticity, hair follicles, sebaceous glands, permeability, protein, and skin thickness.

One object of the present invention is to provide an apparatus and method useful to categorize individuals into skin types and subsequently provide characteristic skin parameters as inputs to an algorithm for minimizing the error of correlation between non-invasive optical analyte measurement and reference analyte measurements. A process of the present invention incorporates the optical characteristics of the individual, using e.g., melanin content, skin thickness, and skin quality, at any region of interest on the surface of the individual skin and categorizes the individual as having these defined characteristics in preparation for subsequent non-invasive detection. The data can be used, for example, for calibration purposes (determining the necessary power level of the radiation source for non-invasive detection) or for compensating for the detected signal.

While some of the skin parameters have a significant, or primary, effect on the correlation, and others are of secondary importance, the error minimization steps described herein can be used to determine the relative importance of these parameters with respect to the measurement of glucose. Each skin parameter is measured either by a physician for input into a glucose monitoring device or can be done by the device and the measurements stored in memory to be used in the algorithm to minimize correlation error.

All relevant skin parameters can be measured using an optical light source, which illuminate in the visible to infrared wavelengths, and a detector sensitive to these wavelengths. The light source can be any source suitable for the intended purpose, such as, a halogen lamp, a laser diode, a laser, or an LED. In a similar manner, the detector is paired with the source and thus can be selected from well known detectors suitable for use with an appropriate light source, e.g., photodiodes, diode arrays, or CCD arrays. Since these two components are typically required components of an optical non-invasive monitoring devices, such as those used to measure glucose, they also provide the capability of measuring skin parameters. The light source is used to probe the region of interest by providing optical flux and the detector is used to collect the flux resulting from the interaction with the patient's skin. The arrangement of the source with respect to the detector determines whether absorbance or reflectance/scattering is the measuring protocol. As will be apparent to those skilled in the art, multiple light sources and detectors can also be utilized to perform these measurements.

Other components, such as, e.g., lenses or fiber optics, are incorporated where necessary to facilitate light transmission and collection. For example, the light sources can be coupled to an optical fiber via SMA connections or focused onto tissue using appropriate lenses. The light source, including lenses and/or an optical fiber is preferably contained within an enclosure capable of mating with skin or receiving extremities (e.g., fingers, ear lobes) for optimal optical coupling into skin.

The radiation source is allowed to interact with the patient tissue and the portion of reflected light is detected using optical fibers or lenses positioned at an appropriate backscattering geometry for optimal collection of reflected light. The power level of the radiation source is controllable using appropriate power sources.

The intensity of the collected light is detected by a detector capable or receiving light within the same region. Exemplary detectors are a CCD detector and a photodiode of a PMT detector for subsequent recording. The CCD and PMT detector can be used in conjunction with a monochromator to distinguish spectral contents depending on the use of a broad-band emission light source.

By positioning optical fibers or lenses opposite the light source with the skin in between, the transmitted light can be recorded in a similar manner. Multiple optical sources and detectors can be used to probe several distinct regions within a defined area of skin for subsequent comparison.

The detected reflected and/or transmitted light intensity from the detectors is converted into digital form for further processing, e.g., by a computer. The data is then used to calculate the absorption and/or scattering coefficient of the skin parameter.

Each skin parameter can be measured according to its optical properties. Skin parameters such as elasticity can be derived from optical measurements of skin constituents such as fat, protein, and skin hydration. Skin parameters such as melanin, hemoglobin, bilirubin, caratenoids, and other chromophores are measured by their absorbance as a function of wavelength. Each skin parameter is distinguished from the other by their extinction coefficient which is wavelength dependent. The value for each skin parameter is determined by Beer's Law which relates absorbance to concentration, extinction coefficient, and path length. Path length can be most easily determined by measuring transmission through a portion of the patient, for example an extremity such as a finger or ear lobe, etc.

It is of course understood that while it is presently preferred that the method of calibration and categorization encompasses a plurality of skin parameters, a single skin parameter may also be utilized in the method and apparatus of the invention.

Thus, the present invention provides a method for the calibration and categorization of human individuals in preparation for in vivo non-invasive detection of biologically significant compounds using non-ionizing radiation. The preferred biologically significant compound to be measured by the present invention is glucose; other biologically significant compounds can also be measured to provide data for use as described here. In one aspect, the present invention provides a process of calibrating an individual in preparation for the non-invasive measurement of an biological compound across the skin of that individual using non-ionizing radiation. In accordance with that process, the contribution of melanin, or other chromophores such as hemoglobin, to the absorption, reflection and/or transmittance of non-ionizing radiation is determined. The subsequent non-invasive measurement of the biological compound is then corrected for the contribution of the chromophore.

Melanin, a chromophore present in the stratum corneum and epidermis layer of human skin, is the only significant structural skin pigment affecting the transmittance properties of skin. Differences in skin melanin content give rise to a wide range of skin colors ranging from "black" to "white".

The contribution of melanin to the absorption, reflection and/or transmittance of non-ionizing radiation is accomplished by determining the absorption and scattering coefficients of melanin. The absorption and scattering coefficients of melanin may be determined with remittance spectroscopy using diffuse reflective measurements of melanin.

The diffuse reflectance measurements are based on the known Kubelka-Munk relations for scattering and absorption coefficients. The ratio of the two coefficients at a given wavelength is a function of the reflectance and transmittance of the radiation source applied to and detected from the tissue medium.

Alternatively, the frequency domain measurements may be used to determine the absorption of melanin by applying a modulated light source to the tissue and detecting the DC and AC components of the photon density wave propagating through tissues as well as the phase shift of the detected signal relative to the source. The absorption coefficient is then calculated using known relations from the detected variables such as described by Sergio Fantini in "Quantitative Determination Of The Absorption Spectra Of Chromophores In Strongly Scattering Media: A Light-Emitting Diode Based Technique".

Remittance spectroscopy is well established and is described in the literature. An article describing a potentially cost-effective way for performing frequency domain measurements using a Light-Emitting Diode (LED) is described by Sergio Fantini in "Quantitative Determination Of The Absorption Spectra Of Chromophores In Strongly Scattering Media: A Light-Emitting Diode Based Technique".

The optical properties of melanin and a method of remittance spectroscopy for obtaining the absorption and scattering coefficients of melanin has been previously described (See. e.g., "The Optics of Human Skin", published by Anderson, R. and Parrish, J.; N. Kolli and A. Baqer, "Spectroscopic Characteristics of Human Nelanin In Vivo", and "On the Assessment of Melanin in Human Skin In Vivo".

By way of example, a calibration and correction process of the present invention uses diffuse reflectance spectroscopy (also known as remittance spectroscopy). The determination of the absorption coefficient of melanin is typically done using nonionizing radiation in the range of 600 nm to 1000 nm. The absorption characteristics of melanin are well defined within this region.

For the measurement of melanin the radiation source can be in the form of a halogen lamp filtered for individual spectral regions of interest or the source can be in the form of a laser diode capable of emitting at a discrete wavelength within the preferred region. Yet another form of radiation source can be in the form of LEDs operating at discrete wavelength ranges within the preferred region.

The detected reflected and/or transmitted light intensity from the detectors is converted into digital form for further processing by, e.g., a computer. The data is used to calculate the absorption and scattering coefficient of melanin according to well known methods.

By way of example, the ratio of absorption-to-scattering coefficient is defined by the equation $t(1+R^2-T^2)/2R]-1$ and the scattering coefficient is: $1/D[K/S(K/S+2)]A-\frac{1}{2}cothA-1tl-R(K/S+1)/R[K/S(K/S+2)]A\frac{1}{2}$. In this equation, t is transmission, S is the scattering coefficient, K is the absorption coefficient, R is reflection and D is the distance of interaction.

A minimum of two different measurements are necessary to determine the values of S and K. Those two measurements can be measurements of reflectance and transmittance or measurements of reflectance at two different locations.

The calculated values of the absorption and scattering coefficients obtained from diffuse reflective or frequency domain measurements are then used to correct subsequent measurements of the biological compound. By way of example, the absorption and scattering coefficients of melanin allow for calculation of the contribution of melanin to the absorbance and scattering of light at other wavelengths which wavelengths are used to detect biological compounds. Means for calculating the contribution of melanin to the absorption or transmittance of light at a given wavelength using the absorption and scattering coefficients of melanin are well known in the art.

As stated above, the process of the present invention includes categorization and correction of non-invasive measurements for other skin parameters.

Skin thickness, a parameter related to path length, can be determined by using time-of-flight measurements with the light source and detector. A short pulse of light from the source is applied to a skin region of interest (such as an extremity) and a detector is positioned opposite or otherwise appropriately placed to collect the arriving light that have traveled through the region of interest. A time profile of arriving light can be plotted from detector intensity values. The slope of the intensity curve vs. time at the front edge is calculated to determine the minimum thickness of the light path. Alternatively, the contribution of skin thickness may be detected using remittance spectroscopy and frequency domain measurements because the absorption coefficient relations are inversely proportional to distance traveled by the non-ionizing radiation.

The quality of the skin such as calluses or other abnormalities can be determined from the remittance measurement due to the change or the index of refraction between air and tissue. The change in index of refraction is characteristic of abnormality and can be determined from the increase or decrease in diffuse reflectance with respect to normal skin. This is measurable using remittance spectroscopy.

The water content of the skin in the region of interest is determined by measuring the characteristic infrared absorbance of water. The amount of water is then calculated based on the optical density of water in the skin region. The extent of hydration in the skin area of interest can also provide the state of permeability of the region which will correlate to the blood flow in the region and the detectable level of analytes. Fat content may also be measured using absorbance. Proteins can be measured using circular polarization through circular dichroism using visible and infrared light. Preferential absorption of right or left circularly polarized light provides a measurement of the amount of a specific protein present in the skin region of interest. Temperature can be measured using infrared absorbance of other skin parameters such as water content and fat content. Water has strong temperature dependent absorbances at specific wavelengths and thus absorbance peaks will shift with respect to temperature. The shifts in absorbance can be used to determine temperature of a skin region of interest.

The skin quality of a specific region is measured by using the light scattering property of the region. The scattering of light is determined partly by the index of refraction. The scattering can be detected using back scattering where a light from the source is applied and a detector placed at an appropriate position to collect the reflected light. The quality of the skin region determines the specific angles that the light will scatter from a surface. The angle distribution of reflected light determines whether the skin region exhibits diffuse reflection or specular reflection.

The flow or velocity of blood is measured by using Doppler scattering from flowing blood cells. The blood velocity is measured from light scattering by providing light at a specific frequency or wavelength from the light source and measuring the shift in frequency or wavelength from the reflected light that have penetrated into a region containing blood flow. The frequency shift is caused by a moving blood cell. The velocity is determined from the frequency shift.

Other skin parameters such as the number of hair follicles and sebaceous glands can be determined by microscopic imaging the skin area of interest using the CCD element of the detection portion of the glucose monitoring device or, alternatively, can be performed at a physician's office. The hair follicles can be counted by capturing the image and using image processing to count the number of follicles per unit area. The sebaceous glands can be stained with appropriate dyes and counted in a similar manner. It is understood that these two skin parameters would probably be omitted from the calibration method of the invention when one makes skin parameter and glucose measurements through a fingernail. The fingernail provides adequate surface to make optical measurements and is thus preferred as the region from which these measurements can be made.

As set forth above, the correction factors for the skin parameters can be programmed into an algorithm for measuring a biological compound.

Values for the skin parameters are preferably collected from a patient by a physician using the optical methods previously described and as summarized in Table 1 using external instrumentation. The correlation data set for the parameters measured are then stored in the memory of the patient monitoring device.

TABLE 1

| Skin Parameters | Measurement Methods |
|---|---|
| melanin | optical absorbance |
| hemoglobin | optical absorbance |

TABLE 1-continued

| Skin Parameters | Measurement Methods |
| --- | --- |
| bilirubin | optical absorbance |
| caratenoids | optical absorbance |
| thickness | time-of-flight |
| water content | optical absorbance |
| fat content | optical absorbance |
| temperature | optical aborbance wavelength shifts |
| quality | optical back-scatter |
| blood flow | optical Doppler velocimetry |
| elasticity | state of hydration/protein & fat content |
| hair follicles | optical imaging and counting |
| sebaceous glands | optical imaging and counting |
| permeability | state of hydration |
| proteins | optical absorbance/polarization |
| amino acids | optical absorbance |

Alternatively, the skin parameter measurements are collected with the patient monitoring device designed to include the necessary hardware to perform the selected measurement(s). This embodiment has the advantage of allowing the patient/user to collect those measurements depending on the need of the patient to compensate for an analyte measurement. For example, if the user becomes tanned during one portion of the year and is contemplating that his or her analyte measurement, e.g., glucose, is drifting in comparison to the values obtained during the winter, then the user can select that a new measurement of, and correction for, melanin since skin pigment changes are related to melanin content. The user can thus "recalibrate" the monitoring device on a periodic basis, for example monthly or weekly, or as needed prior to performing the actual analyte monitoring step. A further embodiment of the patient monitoring device of the invention includes a calibration button on the patient monitoring device which allows the user to perform a measurement of each skin parameter and store the values in memory for immediate or later use when measuring a biologically significant compound (Scheme 3).

The algorithm which minimizes correlation error utilizes the skin type function or optical qualifier function. Both functions incorporate skin parameters raised to some power and constants weighted according to the contribution of each individual skin parameter's role in the effecting the correlation error of the measurement of glucose. In mathematical terms and showing primary parameters:

$$\text{Skin\_Type} = A(\text{Melanin})^{\wedge}1 + B(\text{Hb})^{\wedge}2 + C(\text{Fat\_Content})^{\wedge}3 + D(\text{Temp})^{\wedge}4 + E(\text{Water\_Content})^{\wedge}5 + \ldots + K \quad 1$$

This skin type function will be used to categorize individuals into skin categories. The number of categories are determined by making these measurements on a sufficiently large population, at least one hundred or more individuals.

Several approaches can be used to incorporate the skin parameters to minimize correlation errors of analyte measurement. The skin factor, which contains the skin parameter contributions, can multiply the measured analyte, e.g., glucose, absorbance as function of wavelengths. In mathematical terms:

$$\text{Glucose} = \text{Skin\_Type}[\text{Absorbance}(\lambda)]$$

$$\text{Glucose} = \text{Skin\_Type}[A(\lambda_1) + A(\lambda_2) + A(\lambda_3) + \ldots + A(\lambda_n)] \quad 2\&3$$

An alternative method to incorporate skin parameters to minimize correlation error is to weight the analyte absorbance as a function of wavelength with the skin parameters. In brief mathematical terms (using glucose as an example):

$$\text{Glucose} = A(\lambda_1) A'\beta_1(\text{Melanin}) + A(\lambda_2) B\beta_2(\text{Hb}) + \ldots \quad 4$$

Yet a third method weighs the analyte absorbance at a specific wavelength with the product of two skin parameters. In brief mathematical terms (again using glucose as an example):

$$\text{Glucose} = A(\lambda_1) A'\beta_1(\text{Melanin})^{\wedge}1 \beta_2(\text{Hb})^{\wedge}2 + A(\lambda_1) A'\beta_1(\text{Melanin})^{\wedge}1 \beta_2 C(\text{Fat\_Content})^{\wedge}3 + \ldots$$

In general the analyte measurement is the summation of analyte absorbances at multiple wavelengths multiplying any combinations and/or permutations of skin parameters.

The following steps provide an iterative approach to minimizing the correlation error of the method of the invention.

1. Collect values for each skin parameter
2. Compare magnitude of skin parameters relative to each other
3. Choose weighting coefficients for each skin parameters
4. Calculate Skin Type factor
5. Calculate Glucose (Eq. 2)
6. Correlate optical glucose value with blood glucose reference
7. Repeat step 6 as to satisfy statistical significance
8. Calculate variance
9. Repeat step 3
10. Compare values from Step 8 to previous iteration
11. If the variance is larger than previous iteration, choose a weighting coefficient to lower the variance. If the variance is smaller than the previous iteration, choose a weighting coefficient to continue lowering the variance.
12. Continue with Step 11 until the correlation error is within expectable limits.

Still further, once correction coefficients for certain variables have been established, the levels of those variables can be detected by methods other than diffuse reflective or frequency domain measurements. For example, pulsed ultrasound or torsional extensibility can be used to measure skin thickness and transdermal water losses or impedance measurements can be used to determine skin water content.

An important feature of a process of the present invention is the use of the calibration and correction process on each subject prior to the non-invasive measurement of the biological compound of interest. The calibration and correction process is preferably performed immediately prior to that measurement. Further, the calibration and correction process is carried out on the same area of the skin as the subsequent, non-invasive measurement. In this way, a process of the present invention compensates for subject-to-subject variability as well as for time dependent changes in a particular subject. In other words, the detected values of the biological compound are accurate for that given subject at that particular time.

The present invention has been described with reference to preferred embodiments. One of skill in the art will readily appreciate that changes, alterations and modifications can be made to those embodiments without departing from the true scope and spirit of the invention.

We claim:

1. A process of calibrating an individual in preparation for the non-invasive measurement of a biological compound across the skin of that individual, comprising the steps of:
   (a) determining the contribution of one or more skin parameters to the non-invasive measurement and (b) correcting for the contribution of the one or more skin parameters in the subsequent non-invasive measurement of the biological compound, wherein the skin parameters include at least one member selected from the group consisting of melanin, non-melanin chromophores, skin thickness, water content, fat content, temperature, blood flow, skin quality, skin elasticity, hair follicles, sebaceous glands, permeability, proteins, and amino acids, and wherein the subsequent non-invasive measurement of the biological compound requires non-ionizing radiation.

2. The process of claim 1 wherein the skin parameter is melanin.

3. The process of claim 1 wherein the biological compound is selected from glucose, hemoglobin, lipids, cholesterol or protein.

4. The process of claim 3 wherein the biological compound is glucose.

5. The process of claim 1 wherein the skin parameter is melanin.

6. A process of calibrating an individual in preparation for the non-invasive measurement of a biological compound across the skin of that individual, comprising the steps of:
   (a) determining the contribution of one or more skin parameters to the non-invasive measurement and (b) correcting for the contribution of the one or more skin parameters in the subsequent non-invasive measurement of the biological compound wherein the skin parameter is melanin, wherein the subsequent non-invasive measurement of the biological compound requires non-ionizing radiation, and wherein the contribution of melanin to the absorption and transmittance of non-ionizing radiation is accomplished by determining the absorption and scattering coefficients of melanin.

7. The process of claim 6 wherein the absorption and scattering coefficients of melanin are determined using diffuse reflective or frequency domain measurements of melanin.

8. The process of claim 7 wherein the biological compound is glucose.

9. The process of claim 1 wherein the correction for the biological compound is done immediately before the non-invasive measurement.

10. The process of claim 1 wherein the correction for the biological compound is stored in an instrument.

* * * * *